(12) United States Patent
Del Eckels et al.

(10) Patent No.: US 7,771,653 B2
(45) Date of Patent: *Aug. 10, 2010

(54) EXPLOSIVES TESTER WITH HEATER

(75) Inventors: Joel Del Eckels, Livermore, CA (US); Peter J. Nunes, Danville, CA (US); Randall L. Simpson, Livermore, CA (US); Richard E. Whipple, Livermore, CA (US); J. Chance Carter, Livermore, CA (US); John G. Reynolds, San Ramon, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 388 days.

This patent is subject to a terminal disclaimer.

(21) Appl. No.: 11/593,257

(22) Filed: Nov. 1, 2006

(65) Prior Publication Data

US 2007/0189922 A1    Aug. 16, 2007

Related U.S. Application Data

(63) Continuation-in-part of application No. 11/525,655, filed on Sep. 21, 2006.

(60) Provisional application No. 60/733,150, filed on Nov. 2, 2005.

(51) Int. Cl.
*G01N 33/00* (2006.01)

(52) U.S. Cl. .................... 422/58; 422/55; 422/68.1; 422/99

(58) Field of Classification Search ............... 422/55, 422/58, 68.1, 99
See application file for complete search history.

(56) References Cited

U.S. PATENT DOCUMENTS

| | | | |
|---|---|---|---|
| 5,638,166 A | 6/1997 | Funsten et al. | |
| 5,679,584 A | 10/1997 | Mileaf et al. | |
| 6,470,730 B1 | 10/2002 | Chamberlain | |
| 7,294,306 B2 * | 11/2007 | Haas et al. | 422/58 |
| 2004/0265169 A1 | 12/2004 | Haas et al. | |
| 2005/0101027 A1 | 5/2005 | Haas | |
| 2007/0003435 A1* | 1/2007 | Haas et al. | 422/58 |

* cited by examiner

*Primary Examiner*—Sam P Siefke
(74) *Attorney, Agent, or Firm*—Eddie E. Scott; John H. Lee (57) ABSTRACT

An inspection tester system for testing for explosives. The tester includes a body and a swab unit adapted to be removeably connected to the body. At least one reagent holder and dispenser is operatively connected to the body. The reagent holder and dispenser contains an explosives detecting reagent and is positioned to deliver the explosives detecting reagent to the swab unit. A heater is operatively connected to the body and the swab unit is adapted to be operatively connected to the heater.

27 Claims, 4 Drawing Sheets

EXPLOSIVES TESTER WITH HEATER

CROSS-REFERENCE TO RELATED APPLICATIONS

This invention is a continuation-in-part of copending U.S. patent application Ser. No. 11/525,655 filed Sep. 21, 2006, and titled "Explosives Tester With Heater" the disclosure of which is incorporated herein by reference.

This application claims the benefit of U.S. Provisional Patent Application No. 60/733,150 filed Nov. 2, 2005 and titled "New Methods for Heating the Griess Reagent Reaction." U.S. Provisional Patent Application No. 60/733,150 filed Nov. 2, 2005 and titled "New Methods for Heating the Griess Reagent Reaction" is incorporated herein by this reference. The following applications contain related subject matter and are owned by the common assignee, Lawrence Livermore National Security, LLC for the operation of Lawrence Livermore National Laboratory: U.S. patent application Ser. No. 11/208,482, Filed Aug. 18, 2005 for colorimetric chemical analysis sampler for the presence of explosives; U.S. patent application Ser. No. 11/165,474, Filed Jun. 22, 2005, for Chemical Analysis Coupon for the Presence of Explosives; U.S. patent application Ser. No. 11/158,480, Filed Jun, 21,2005 for Chemical Analysis Kit for the Presence of Explosives; U.S. patent application Ser. No. 11/159,452, Filed Jun. 22, 2005 for Spot Test Kit for Explosives Detection; and U.S. patent application Ser. No. 11/634,784, Filed Dec. 05, 2006 for Low to Moderate Temperature Nanolaminate Heater; which are incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to explosives and more particularly to testing for the presence of explosives.

2. State of Technology

U.S. Pat. No. 5,638,166 for an apparatus and method for rapid detection of explosives residue from the deflagration signature thereof issued Jun. 10, 1997 to Herbert O. Funsten and David J. McComas and assigned to The Regents of the University of California provides the following state of the art information: "Explosives are a core component of nuclear, biological, chemical and conventional weapons, as well as of terrorist devices such as car, luggage, and letter bombs. Current methods for detecting the presence of explosives include vapor detection, bulk detection, and tagging. However, these methods have significant difficulties dependent upon the nature of the signature that is detected. . . . It is known that surfaces in contact with explosives (for example, during storage, handling, or device fabrication) will readily become contaminated with explosive particulates as a result of their inherent stickiness. This phenomenon is illustrated in studies that show large persistence of explosives on hands, even after several washings (J. D. Twibell et al., 'Transfer of Nitroglycerine to Hands During Contact with Commercial Explosives,' J. Forensic Science 27 (1982) 783; J. D. Twibell et al., 'The Persistence of Military Explosives on Hands,' J. Forensic Science 29 (1984)284). Furthermore, cross contamination in which a secondary surface is contaminated by contact with a contaminated primary surface can also readily occur. For example, a measurable amount of ammonium nitrate (AN) residue has been found on the lease documents for a rental truck, and significant amounts of the explosives PETN (pentaerythritol tetranitrate) and/or AN have been found on clothing and inside vehicles of suspects in two well-publicized bombings. Therefore, explosive residue will likely persist in large amounts on the explosive packaging and environs, as well as on the individuals involved in building the explosive device, which can provide an avenue for detection of the presence of explosives."

U.S. Pat. No. 5,679,584 for a method for chemical detection issued Oct. 2, 1997 to Daryl Sunny Mileaf and Noe Esau Rodriquez, II provides the following state of the art information: "a method for detecting a target substance which includes collecting a substance sample; introducing the substance sample into a substance card having at least one preselected reagent responsive to the presence of the target substance and having a light-transmissive chamber; and inserting the substance card into a substance detector device having a photosensor and adapted to receive the substance card. Once the substance detector card has been inserted into the substance detector, the method continues by mixing the substance sample with the preselected reagents for a preselected mixing period, thus producing a measurand having a target substance reaction."

U.S. Pat. No. 6,470,730 for a dry transfer method for the preparation of explosives test samples issued Oct. 29, 2002 to Robert T. Chamberlain and assigned to The United States of America as represented by the Secretary of Transportation provides the following state of the art information: " . . . method of preparing samples for testing explosive and drug detectors of the type that search for particles in air. A liquid containing the substance of interest is placed on a flexible Teflon® surface and allowed to dry, then the Teflon® surface is rubbed onto an item that is to be tested for the presence of the substance of interest. The particles of the substance of interest are transferred to the item but are readily picked up by an air stream or other sampling device and carried into the detector."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The ability to identify unknown explosives is of utmost importance to the military, law enforcement and Homeland Security forces worldwide. Spot tests for the identification of explosives have been used in combination with thin-layer chromatography and in forensic analysis. There are some commercial companies (Mistral, Securesearch, Duram products) that produce explosives identification kits. They incorporate color reagents and are used by the military and law-enforcement agencies. They allow the identification of nitroaromatics, nitramines, ammonium nitrate, and recently the potassium chlorate-based explosives. Ex-spray and Duram products are two of the companies. Their systems are available as spray kits or solution-drop kits.

The present invention provides an inspection tester system for testing for explosives. The system comprises a body, a swab unit adapted to be removeably connected to the body, at least one explosives detecting reagent, at least one reagent holder and dispenser operatively connected to the body, the at least one reagent holder and dispenser containing the at least one explosives detecting reagent and positioned to deliver the at least one explosives detecting reagent to the swab unit, and a heater operatively connected to the body, wherein the swab unit is adapted to be operatively connected to the heater.

In one embodiment, the at least one explosives detecting reagent is the Griess reagent. The key to some of the explosive testing kits described above is the Griess reagent. Known since 1879, the Griess reagent reacts with nitrogen oxide compounds, whether bound or free, and produces a highly colored compound that can be used for visible detection. This compound has been shown to be an effective indicator for not only high explosives, but other source of nitrogen oxides, such as biological systems.

The Griess reagent reacts adequately with several high explosives when the explosives are at high concentrations. At low concentrations however, the Griess reagent requires heating to drive the reaction for detection. Heating can easily be done in the laboratory setting with standard laboratory equipment such as a hot plate. This heating is a limiting factor in using this reaction for detection when designing field usable equipment. In existing field portable detection technology, either the heating step must be accomplished or low detection limits are simply not achievable. Most field kits have realized much higher detection limits to retain simplicity, cost, and portability. A few have resorted to resistive heating with fairly large heating unit components, limiting portability and increasing costs.

To enable the Griess reagent to be used in very small, field portable, user friendly systems that are relatively low cost, innovative heating methods have been developed for the technology. These heating methods are departures from the standard laboratory resistive heating technology that is commonly used. They embody redesign of various forms of heating, resistive, combustion, and/or chemical for application to small field used detection systems. Both portability and ease of use are greatly improved with these new innovative designs and techniques.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to FIGS. 1-5 of the drawings, one embodiment of an inspection tester for explosives constructed in accordance with the present invention is illustrated. This embodiment of the present invention is designated generally by the reference numeral 100. The inspection tester 100 is an all-inclusive, inexpensive, and disposable device. The inspection tester can be used anywhere as a primary screening tool by non-technical personnel to determine whether a surface contains explosives. The inspection tester 100 is particularly useful to first responders, military, law enforcement and Homeland Security personnel.

Figure 1:
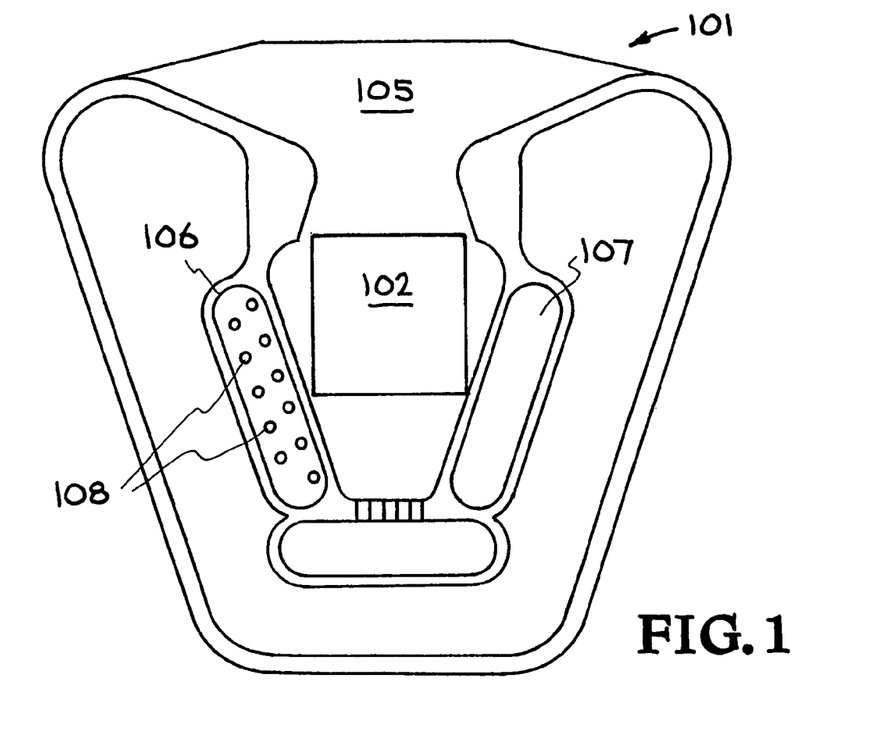
FIG. 1 illustrates one embodiment of an inspection tester for explosives constructed in accordance with the present invention.
Figure 2:
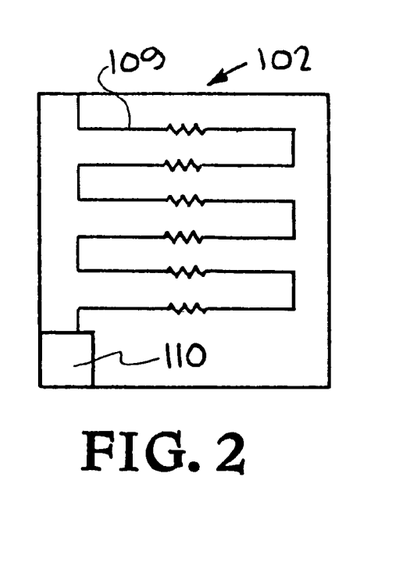
FIG. 2 shows a heater used in the inspection tester body.
Figure 3:
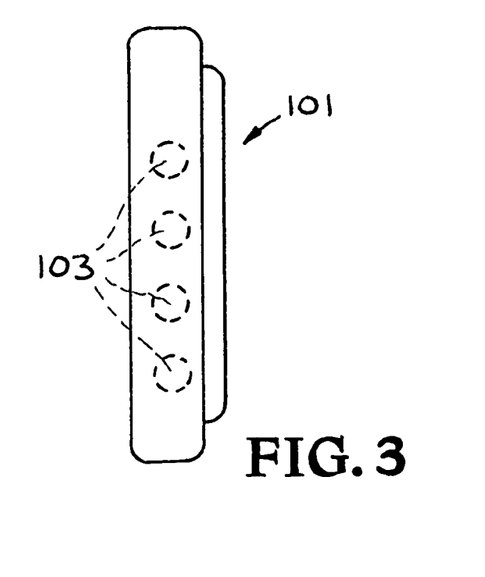
FIG. 3 shows a side view of the inspection tester body and batteries used in connection with the heater.
Figure 4:
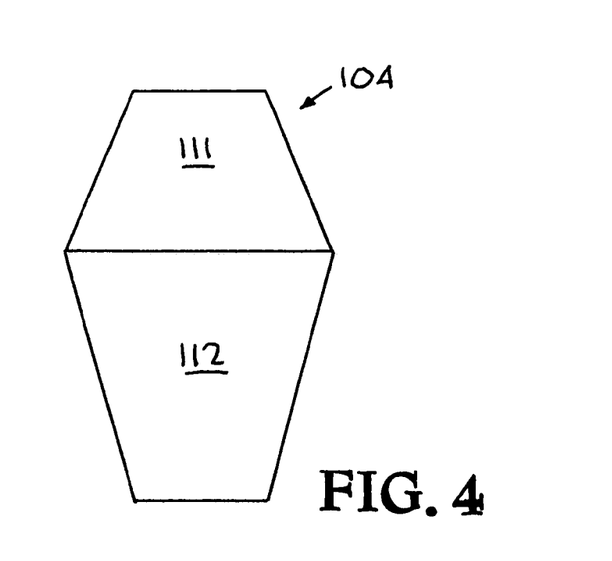
FIG. 4 shows the swab unit sample pad used with the inspection tester body.
Figure 5:
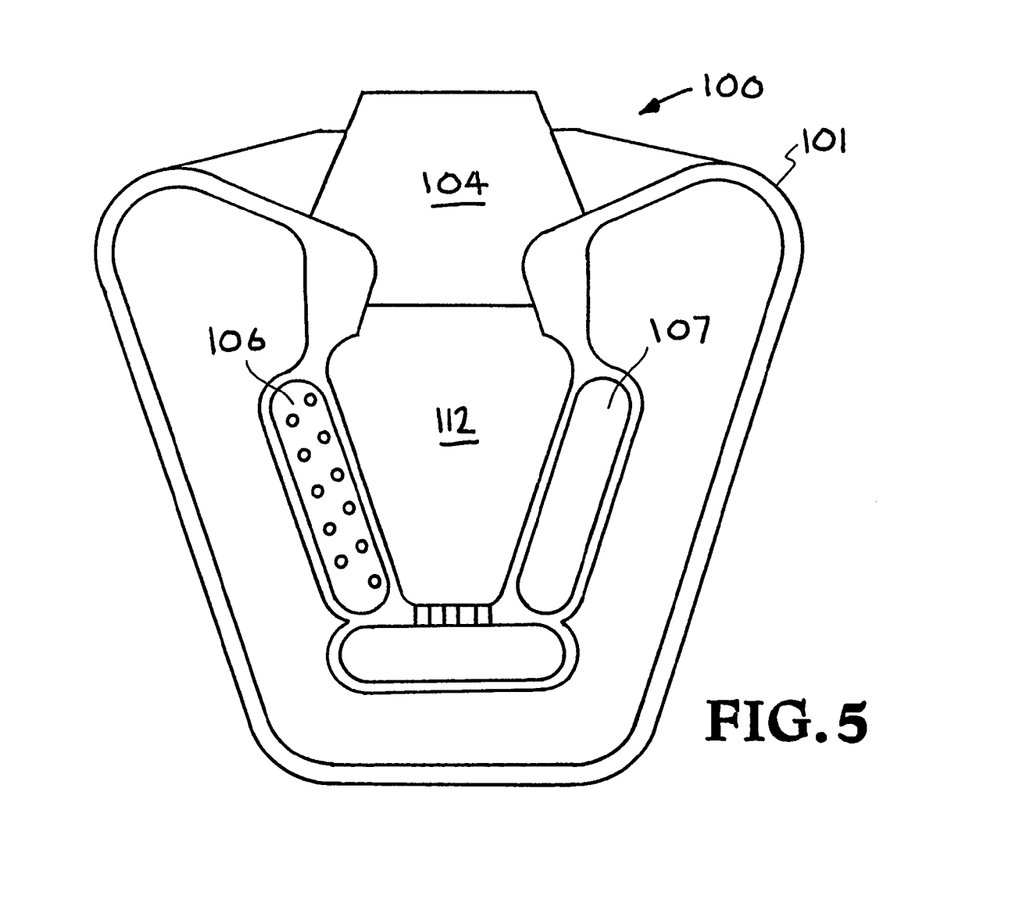
FIG. 5 shows the swab unit sample pad in position in the inspection tester body for testing a sample.

The inspection tester 100 comprises an explosives tester body 101 and a removable swab unit 104 adapted to be removably positioned in the explosives tester body 101. FIG. 1 shows the inspection tester body 101. FIG. 2 shows the heater 102 used in the inspection tester body 101. FIG. 3 shows a side view of the inspection tester body 101 and show batteries 103 used in connection with the heater 102. FIG. 4 shows the swab unit sample pad 104 used with the inspection tester body 101. FIG. 5 shows the swab unit sample pad 104 in position in the inspection tester body 101 for testing a sample.

The inspection tester 100 provides a small, disposable, one use system. The inspection tester 100 uses a simple and rapid method of operation. The removable swab unit sample pad 104 shown in FIG. 4 is exposed to a suspect substance. This may be accomplished by the swab unit sample pad 104 being swiped across a surface containing the suspect substance or the swab unit pad 104 may be exposed to the suspect substance in other ways such as adding the suspect substance to the swab unit sample pad 104. The swab unit sample pad 104 is then placed in the inspection tester body 101 for testing a sample as shown in FIG. 5.

Referring again to FIG. 1, the explosives tester body 101 is a thin flat body that can be described as a card. The card body 101 is made of a suitable material such as paper, wood, plastic, glass, or other suitable material. The explosives tester body 101 is thin and is less than one fourth inch thick. The explosives tester body 101 shown in FIG. 1 is less than one fourth inch thick. The explosives tester body 101 includes a docking entry and retention portion 105 for easy docking of the removable swab unit sample pad 104. The heater 102 is located in the docking entry and retention portion 105 so that the removable swab unit 104 will be positioned directly over the heater 102 when the removable swab unit 104 is placed in position for testing a sample. The explosives tester body 101 also includes ampoule A 106 and ampoule B 107. In various embodiments, ampoule A 106 and ampoule B 107 are breakable ampoules, breakable glass ampoules, squeezable ampoules, and other types of ampoules. As illustrated in FIG. 1, ampoule A 106 includes indentations 108 on the chamber which keeps glass pieces from adhering to the walls.

Referring again to FIG. 2, the heater 102 used in the inspection tester body 101 is shown in greater detail. The heater 102 is a resistive heater with a heating element 109 that changes temperature due to resistance and a controller that regulates the heating and keeps the system from over heating, as well as indicating when the appropriate temperature has been reached. Other resistive heating elements can be used for the heater 102. The key part of the heater 102 is that the heating unit utilizes electrical resistance that generates heat.

Referring again to FIG. 3, a side view of the inspection tester body 101 is shown and the batteries 103 that are used in connection with the heater 102 are illustrated. The heater 102 has a heating element that changes temperature due to resistance, a controller that regulates the heating and keeps the system from over heating, as well as indicating when the appropriate temperature has been reached; a power source, in this case a battery pack 103, but in alternate schemes a step down system from household power can be used; a switch to control the system. Other designs include resistive heater coils placed directly into the explosives tester body 101 with wire leads to an external power supply such as a battery pack.

Referring again to FIG. 4, the removable swab unit 104 is shown in greater detail. A tab area 111 is provided so that the swab unit 104 can be easily inserted and removed from the explosives tester body 101. The removable swab unit 104 includes a color reaction area 112. The color reaction area 112 can be a lateral flow membrane. The lateral flow membrane 112 comprises a microporous membrane that provides migration of fluids from ampoule A 106 and fluids from ampoule B 107. Lateral flow membranes are known for their use in other fields such as blotting techniques, enzyme-linked immunosorbent assay (ELISA) testing, and lateral-flow immunochromatographic tests. The lateral flow membrane is a Porex Lateral-Flo Membrane. The lateral flow membrane comprises polyethylene spheres fused into a Lateral-Flo™ membrane. Applicants experimentally determined that the properties of Porex make it an ideal swipe material for the inspection tester 100. The lateral flow membrane is chemical resistant, withstands heat as high as 130° C., is durable, is inexpensive, can be cut to any size, and concentrates suspect materials along the solvent front making calorimetric detection limits. The lateral flow membrane provides a high surface area swipe for sample collection.

Referring again to FIG. 5, the operation of the explosives tester 100 will be described. The removable swab unit 104 is shown positioned in the explosives tester body 101. The heating element of the heater 102 is activated and the removable swab unit 104 will be heated as hereinafter described.

Ampoule A 106 and ampoule B 107 provide two reagent activation units. Ampoule A 106 (for reagent A) and ampoule B 107 (for reagent B) are operatively mounted on the explosives tester body 101. The ampoule A 106 containing the first explosives detecting reagent A is positioned to deliver the first explosives detecting reagent A to the color reaction area 112 of the removable swab unit 104. The Ampoule B 107 containing the second explosives detecting reagent B is positioned to deliver the second explosives detecting reagent B to the color reaction area 112 of the removable swab unit 104. The reagent A contains Meisenheimer complexes. The reagent B provides a Griess reaction. The Meisenheimer complexes and Griess reaction are well known in the art and need not be described here.

The inspection tester 100 uses a simple and rapid procedure summarized by the following four step operation:

STEP 1) A suspect surface is swiped with the removable swab unit sample pad 104. This may be accomplished by the swab unit sample pad 104 being swiped across a surface containing the suspect substance or the swab unit pad 104 may be exposed to the suspect substance in other ways such as adding the suspect substance to the swab unit sample pad 104. This will cause any explosives residue to be collected and held by the swab unit sample pad 104.

STEP 2) The breakable or squeezable ampoule A 106 is located in a position to deliver the first explosives detecting reagent A to the color reaction area 112 of the removable swab unit 104. The breakable or squeezable ampoule A 106 is pressed to break or squeeze it thereby dispensing reagent A onto the color reaction area 112 of the removable swab unit 104. The regent A contacts any explosives residue that has been collected by the swab unit sample pad 104. The color reaction area 112 of the removable swab unit 104 concentrates suspect materials along the solvent front. If the swab unit sample pad 104 becomes colored, the test is positive for explosives. If no color appears the test for explosives is negative to this point.

STEP 3) If STEP 2 is negative to this point, the heater 102 is activated. This causes the swab unit sample pad 104, reagent A, and any explosives residue to become heated. If the swab unit sample pad 104 now becomes colored, the test is positive for explosives. If no color appears the test for explosives is negative to this point.

STEP 4) The breakable or squeezable ampoule B 107 is located in a position to deliver the second explosives detecting reagent B to the color reaction area 112 of the removable swab unit 104. If STEP 3 is negative to this point, the breakable or squeezable ampoule B 107 is pressed to brake or squeeze it thereby dispensing reagent B onto the color reaction area 112 of the removable swab unit 104. The regent B contacts any explosives residue that has been collected by the swab unit sample pad 104. The color reaction area 112 of the removable swab unit 104 concentrates suspect materials along the solvent front. If the swab unit sample pad 104 becomes colored, the test is positive for explosives. If no color appears the test for explosives is negative to this point.

STEP 5) If STEP 4 is negative to this point, the heater 102 is activated. This causes the swab unit sample pad 104, reagent B, and any explosives residue to become heated. If the swab unit sample pad 104 now becomes colored, the test is positive for explosives. If no color appears the test for explosives is negative.

The inspection tester 100 provides a simple, chemical, field spot-test by to provide a rapid screen for the presence of a broad range of explosive residues. The lateral flow membrane of the color reaction area 112 of the removable swab unit 104 is microporous cellulose nitrate membrane that provides migration of the fluids from ampoule A 106 and ampoule B 107. The lateral flow membrane concentrates suspect materials along the solvent front. This concentration makes the explosives tester 100 more sensitive because by concentrating any explosives particles along the solvent front a larger amount of materials in one place. The color that will be produced by the reagents from ampoule A 106 and ampoule B 107 will be easier to see.

The inspection tester 100 is fast, extremely sensitive, low-cost, very easy to implement, and provides a very low rate of false positives. The inspection tester for explosives 100 provides a fast, sensitive, low-cost, very easy to implement system for testing the suspected packages. The inspection tester for explosives 100 is inexpensive and disposable. The inspection tester for explosives 100 has detection limits between 0.1 to 100 nanograms, depending on the type of explosives present. A large number of common military and industrial explosives can be easily detected such as HMX, RDX, NG, TATB, Tetryl, PETN, TNT, DNT, TNB, DNB and NC. The inspection tester 100 is small enough that a number of them can fit in a pocket or brief case.

Figure 6:
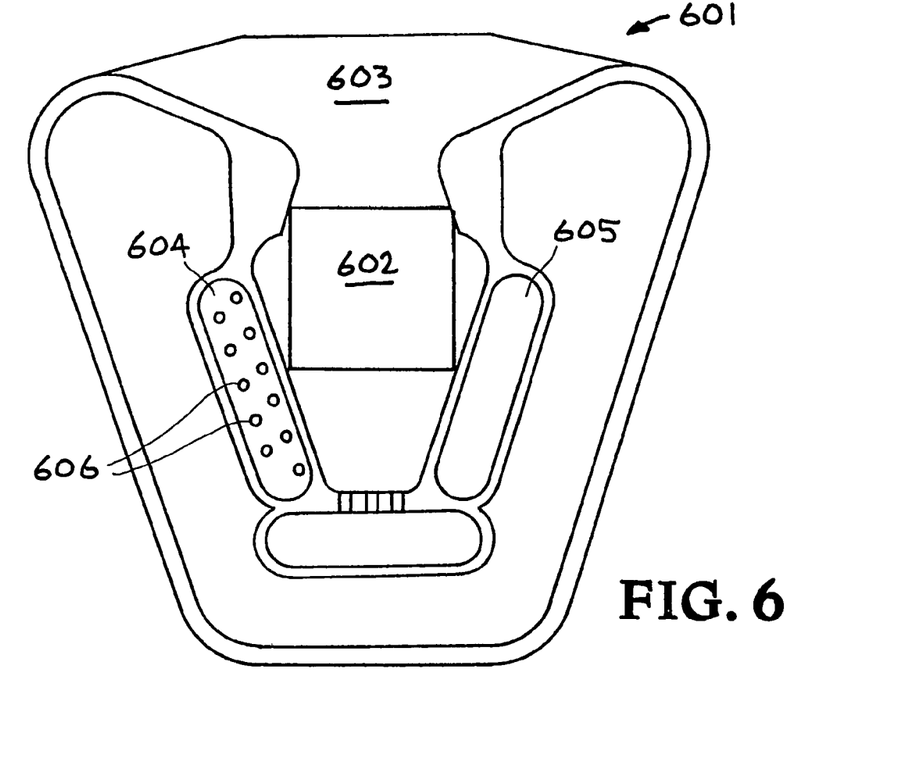
FIG. 6 illustrates another embodiment of an inspection tester for explosives constructed in accordance with the present invention.

Referring now to FIG. 6, another embodiment of an inspection tester for explosives constructed in accordance with the present invention is illustrated. This embodiment of the present invention is designated generally by the reference numeral 600. The inspection tester 600 is an all-inclusive, inexpensive, and disposable device. The inspection tester can be used anywhere as a primary screening tool by non-technical personnel to determine whether a surface contains explosives. The inspection tester 600 is particularly useful to first responders, military, law enforcement and Homeland Security personnel.

The inspection tester 600 comprises an explosives tester body 601 and a removable swab unit, such as the swab unit shown in FIG. 4, adapted to be removably positioned in the explosives tester body 601. A heater 602 is located in the inspection tester body 601.

The heater 602 is a heater that operates through chemical heating. The key part of this heat 602 is that chemical reactions generate the heat. The heater 602 is shown in greater detail in FIG. 7. The heater 602 is made of a nanolaminate chemical heating unit. A sandwich of aluminum 603 and nickel 604 have nanolaminate chemical heating material 605 inserted between the two pieces of metal to form an Al/Ni nanolaminate chemical heating unit. In this design, nanolaminate material 605 is inserted between the two pieces of metal to distribute the heat. This metal composite is then placed in the inspection tester body 601 in the docking and entry portion and will be located under the removable swab unit.

Figure 7:
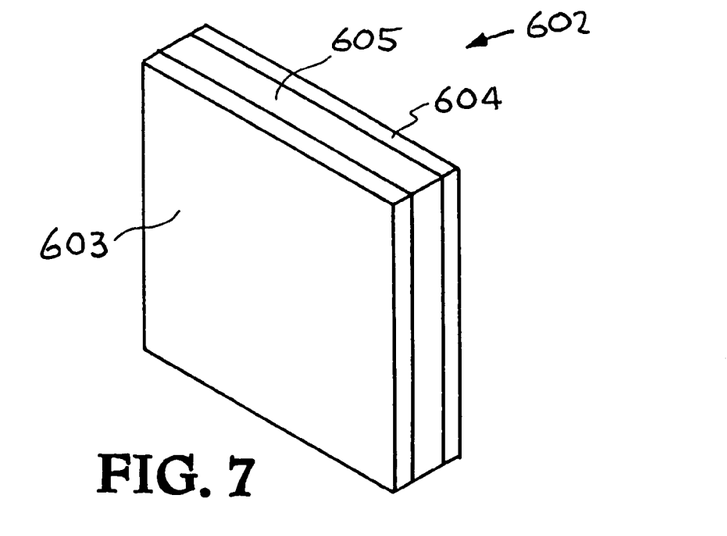
FIG. 7 shows a heater used in the inspection tester body.

When the heating is needed, the nano-laminate is activated, generating heat that is distributed to the system. The nano-laminate configuration is one example of chemical heating. Other types that can be used in various designs for the detection system are chemical heating such as chemical hand warmers, chemical food warmers, etc.

In one embodiment of heater 602 illustrated in FIG. 7, an energetic nano-laminate material 605 is initiated by directing an electrical current through the energetic nanolaminate 605. The system provides a system for bonding materials 603, 604, and 605. A first block 605 is bonded to a blocks 603 and 604. A solder, brazing material, or other form of bonding material that is activated by heat is positioned between the first block 605 and the blocks 603 and 604. For example, a first solder, brazing material, or other form of bonding material that is activated by heat and a second solder, brazing material, or other form of bonding material that is activated by heat are positioned between the first block 605 and the blocks 603 and 604.

Referring again to FIG. 6, the operation of the explosives tester 600 will be described. The removable swab unit is shown positioned in the explosives tester body 601. The chemical heating element of the heater 602 is activated and the removable swab unit will be heated as hereinafter described.

Ampoule A 606 and ampoule B 607 provide two reagent activation units. Ampoule A 606 (for reagent A) and ampoule B 607 (for reagent B) are operatively mounted on the explosives tester body 601. The ampoule A 606 containing the first explosives detecting reagent A is positioned to deliver the first explosives detecting reagent A to the color reaction area 612 of the removable swab unit 604. The Ampoule B 607 containing the second explosives detecting reagent B is positioned to deliver the second explosives detecting reagent B to the color reaction area of the removable swab unit. The reagent A contains Meisenheimer complexes. The reagent B provides a Griess reaction. The Meisenheimer complexes and Griess reaction are well known in the art and need not be described here.

The inspection tester 600 uses a simple and rapid procedure summarized by the following four step operation:

STEP 1) A suspect surface is swiped with the removable swab unit sample pad 604. This may be accomplished by the swab unit sample pad being swiped across a surface containing the suspect substance or the swab unit pad may be exposed to the suspect substance in other ways such as adding the suspect substance to the swab unit sample pad. This will cause any explosives residue to be collected and held by the swab unit sample pad.

STEP 2) The breakable or squeezable ampoule A 606 is located in a position to deliver the first explosives detecting reagent A to the color reaction area of the removable swab unit. The breakable or squeezable ampoule A 606 is pressed to break or squeeze it thereby dispensing reagent A onto the color reaction area of the removable swab unit. The regent A contacts any explosives residue that has been collected by the swab unit sample pad. The color reaction area of the removable swab unit concentrates suspect materials along the solvent front. If the swab unit sample pad becomes colored, the test is positive for explosives. If no color appears the test for explosives is negative to this point.

STEP 3) If STEP 2 is negative to this point, the heater 602 is activated. This causes the swab unit sample pad, reagent A, and any explosives residue to become heated. If the swab unit sample pad now becomes colored, the test is positive for explosives. If no color appears the test for explosives is negative to this point.

STEP 4) The breakable or squeezable ampoule B 607 is located in a position to deliver the second explosives detecting reagent B to the color reaction area of the removable swab unit. If STEP 3 is negative to this point, the breakable or squeezable ampoule B 607 is pressed to brake or squeeze it thereby dispensing reagent B onto the color reaction area of the removable swab unit. The regent B contacts any explosives residue that has been collected by the swab unit sample pad. The color reaction area of the removable swab unit concentrates suspect materials along the solvent front. If the swab unit sample pad becomes colored, the test is positive for explosives. If no color appears the test for explosives is negative to this point.

STEP 5) If STEP 4 is negative to this point, the heater 602 is activated. This causes the swab unit sample pad, reagent B, and any explosives residue to become heated. If the swab unit sample pad now becomes colored, the test is positive for explosives. If no color appears the test for explosives is negative.

The inspection tester 600 provides a simple, chemical, field spot-test by to provide a rapid screen for the presence of a broad range of explosive residues. The lateral flow membrane of the color reaction area of the removable swab unit is microporous cellulose nitrate membrane that provides migration of the fluids from ampoule A 606 and ampoule B 607. The lateral flow membrane concentrates suspect materials along the solvent front. This concentration makes the explosives tester 600 more sensitive because by concentrating any explosives particles along the solvent front a larger amount of materials in one place. The color that will be produced by the reagents from ampoule A 606 and ampoule B 607 will be easier to see.

The inspection tester 600 is fast, extremely sensitive, low-cost, very easy to implement, and provides a very low rate of false positives. The inspection tester for explosives 600 provides a fast, sensitive, low-cost, very easy to implement system for testing the suspected packages. The inspection tester for explosives 600 is inexpensive and disposable. The inspection tester for explosives 600 has detection limits between 0.1 to 100 nanograms, depending on the type of explosives present. A large number of common military and industrial explosives can be easily detected such as HMX, RDX, NG, TATB, Tetryl, PETN, TNT, DNT, TNB, DNB and NC. The inspection tester 600 is small enough that a number of them can fit in a pocket or brief case.

Figure 8:
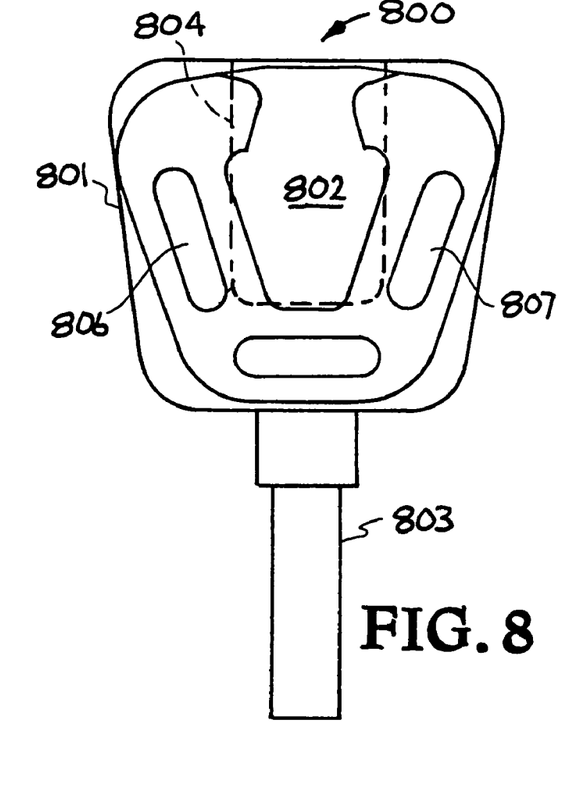
FIG. 8 illustrates another embodiment of an inspection tester for explosives constructed in accordance with the present invention.

Referring now to FIG. 8, another embodiment of an inspection tester for explosives constructed in accordance with the present invention is illustrated. This embodiment of the present invention is designated generally by the reference numeral 800. The inspection tester 800 is an all-inclusive, inexpensive, and disposable device. The inspection tester can be used anywhere as a primary screening tool by non-technical personnel to determine whether a surface contains explosives. The inspection tester 800 is particularly useful to first responders, military, law enforcement and Homeland Security personnel.

The inspection tester 800 comprises an explosives tester body 801 and a removable swab unit 802, such as the swab unit shown in FIG. 4, adapted to be removably positioned in the explosives tester body 801. A heater 803 is located in connection with the inspection tester body 801. The heater 803 is a combustion heating system. The outline of a heat transfer area 804 is shown on the explosives tester body 801 beneath the removable swab unit 802.

Figure 9:
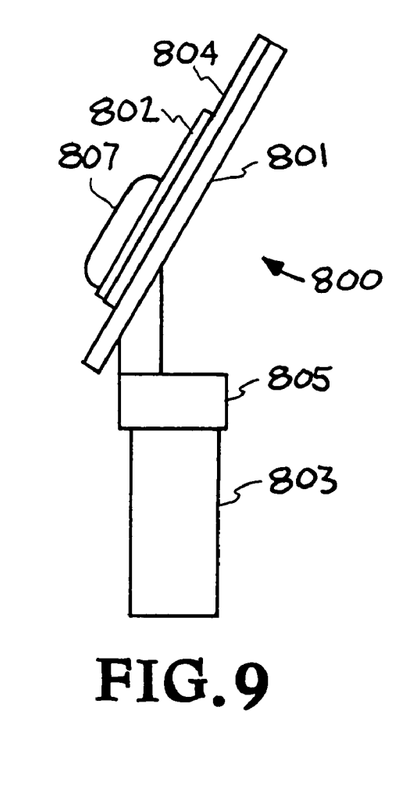
FIG. 9 shows a side view of the inspection tester.

Referring now to FIG. 9, a side view of the inspection tester 800 is shown. The combustion heater 803 is located in connection with the inspection tester body 801. The combustion heater 803 heats the heat transfer area 804. The combustion heater 803, illustrated in FIGS. 8 and 9, has a combustion-heating source, in this case a cigarette lighter. It is understood that any commercial or specially designed combustion source can be used. The key part of the heater 803 system is that combustion generates the heat. The combustion source 803 is in contact with the heat distributor 804 that distributes the heat to the swab unit 802. A temperature indicator strip is attached to enable monitoring of the heat. The lighter 803 is placed in a plastic framework 805 that positions it at the appropriate angle and distance from the heat distributor 804. In this design, the lighter 803 is used. However, this is not to limit the source of combustion heat. Other systems such as combustion hand warmers, food warmers, for example can also be used.

Referring again to FIG. 8, the operation of the explosives tester 800 will be described. The removable swab unit 802 is shown positioned in the explosives tester body 801. The heater 803 is activated and the removable swab unit will be heated as hereinafter described.

Ampoule A 806 and ampoule B 807 provide two reagent activation units. Ampoule A 806 (for reagent A) and ampoule B 807 (for reagent B) are operatively mounted on the explosives tester body 801. The ampoule A 806 containing the first explosives detecting reagent A is positioned to deliver the first explosives detecting reagent A to the color reaction area 812 of the removable swab unit 804. The Ampoule B 807 containing the second explosives detecting reagent B is positioned to deliver the second explosives detecting reagent B to the color reaction area of the removable swab unit. The reagent A contains Meisenheimer complexes. The reagent B provides a Griess reaction. The Meisenheimer complexes and Griess reaction are well known in the art and need not be described here.

The inspection tester 800 uses a simple and rapid procedure summarized by the following four step operation:

STEP 1) A suspect surface is swiped with the removable swab unit sample pad 804. This may be accomplished by the swab unit sample pad being swiped across a surface containing the suspect substance or the swab unit pad may be exposed to the suspect substance in other ways such as adding the suspect substance to the swab unit sample pad. This will cause any explosives residue to be collected and held by the swab unit sample pad.

STEP 2) The breakable or squeezable ampoule A 806 is located in a position to deliver the first explosives detecting reagent A to the color reaction area of the removable swab unit. The breakable or squeezable ampoule A 806 is pressed to break or squeeze it thereby dispensing reagent A onto the color reaction area of the removable swab unit. The regent A contacts any explosives residue that has been collected by the swab unit sample pad. The color reaction area of the removable swab unit concentrates suspect materials along the solvent front. If the swab unit sample pad becomes colored, the test is positive for explosives. If no color appears the test for explosives is negative to this point.

STEP 3) If STEP 2 is negative to this point, the heater 803 is activated. This causes the swab unit sample pad, reagent A, and any explosives residue to become heated. If the swab unit sample pad now becomes colored, the test is positive for explosives. If no color appears the test for explosives is negative to this point.

STEP 4) The breakable or squeezable ampoule B 807 is located in a position to deliver the second explosives detecting reagent B to the color reaction area of the removable swab unit. If STEP 3 is negative to this point, the breakable or squeezable ampoule B 807 is pressed to brake or squeeze it thereby dispensing reagent B onto the color reaction area of the removable swab unit. The regent B contacts any explosives residue that has been collected by the swab unit sample pad. The color reaction area of the removable swab unit concentrates suspect materials along the solvent front. If the swab unit sample pad becomes colored, the test is positive for explosives. If no color appears the test for explosives is negative to this point.

STEP 5) If STEP 4 is negative to this point, the heater 803 is activated. This causes the swab unit sample pad, reagent B, and any explosives residue to become heated. If the swab unit sample pad now becomes colored, the test is positive for explosives. If no color appears the test for explosives is negative.

The inspection tester 800 provides a simple, chemical, field spot-test by to provide a rapid screen for the presence of a broad range of explosive residues. The lateral flow membrane of the color reaction area of the removable swab unit is microporous cellulose nitrate membrane that provides migration of the fluids from ampoule A 806 and ampoule B 807. The lateral flow membrane concentrates suspect materials along the solvent front. This concentration makes the explosives tester 800 more sensitive because by concentrating any explosives particles along the solvent front a larger amount of materials in one place. The color that will be produced by the reagents from ampoule A 806 and ampoule B 807 will be easier to see.

The inspection tester 800 is fast, extremely sensitive, low-cost, very easy to implement, and provides a very low rate of false positives. The inspection tester for explosives 800 provides a fast, sensitive, low-cost, very easy to implement system for testing the suspected packages. The inspection tester for explosives 800 is inexpensive and disposable. The inspection tester for explosives 800 has detection limits between 0.1 to 100 nanograms, depending on the type of explosives present. A large number of common military and industrial explosives can be easily detected such as HMX, RDX, NG, TATB, Tetryl, PETN, TNT, DNT, TNB, DNB and NC. The inspection tester 800 is small enough that a number of them can fit in a pocket or brief case.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An inspection tester apparatus for testing a suspect material for explosives, comprising:
    a body made of paper, wood, plastic, or glass, wherein said body has a thickness that is less than one fourth inch,
    a docking entry and retention structure that forms a portion of said body,
    a swab unit adapted to be removeably connected to said docking entry and retention structure of said body,
    at least one explosives detecting reagent,
    at least one reagent holder and dispenser operatively connected to said body, said at least one reagent holder and dispenser containing said at least one explosives detecting reagent and positioned to deliver said at least one explosives detecting reagent to said swab unit when said swab unit is connected to said docking entry and retention structure, and
    a heater operatively connected to said body and located in said docking entry and retention structure of said body, wherein said swab unit is connected to said docking entry and retention structure and is directly over said heater and operatively connected to said heater.

2. The inspection tester apparatus for testing for explosives of claim 1 wherein said heater is a resistance heater.

3. The inspection tester apparatus for testing for explosives of claim 1 wherein said heater is a resistance heater that includes a resistance heating coil and a controller.

4. The inspection tester apparatus for testing for explosives of claim 1 wherein said heater is a chemical heater.

5. The inspection tester apparatus for testing for explosives of claim 1 wherein said heater is a chemical heater with a nanolaminate chemical heating element.

6. The inspection tester apparatus for testing for explosives of claim 1 wherein said heater is a chemical heater with an aluminum and nickel nanolaminate chemical heating element.

7. The inspection tester apparatus for testing for explosives of claim 1 wherein said heater is a combustion heater.

8. The inspection tester apparatus for testing for explosives of claim 1 wherein said heater is a combustion heater comprising a lighter and a connector connecting said lighter to said body.

9. The inspection tester apparatus for testing for explosives of claim 1 wherein said at least one explosives detecting reagent comprises a Griess reagent.

10. The inspection tester apparatus for testing for explosives of claim 1 wherein said at least one reagent holder and dispenser comprises an ampoule.

11. The inspection tester apparatus for testing for explosives of claim 1 wherein said at least one reagent holder and dispenser comprises a breakable ampoule.

12. The inspection tester apparatus for testing for explosives of claim 1 wherein said at least one reagent holder and dispenser comprises a breakable glass ampoule.

13. The inspection tester apparatus for testing for explosives of claim 1 wherein at least one reagent holder and dispenser comprises a breakable glass ampoule with indentations on said breakable glass ampoule.

14. An inspection tester apparatus for testing a suspect material for explosives, comprising:
    a body made of paper, wood, plastic, or glass, said body being less than one fourth inch thick,
    a docking entry and retention structure that forms a portion of said body,
    a swab unit adapted to be removeably positioned in said docking entry and retention structure of said body, said swab unit made of microporous lateral flow membrane material wherein said microporous lateral flow membrane material produces a solvent front and concentrates the suspect material along said solvent front,
    at least one explosives detecting reagent,
    at least one reagent holder and dispenser operatively connected to said body, said at least one reagent holder and dispenser containing said at least one explosives detecting reagent and positioned to deliver said at least one explosives detecting reagent to said swab unit when said swab unit is connected to said docking entry and retention structure, and
    a heater located in said docking and entry structure of said body, wherein said swab unit is operatively connected to said heater when said swab unit is connected to said docking entry and retention structure said swab unit is positioned directly over said heater in said docking entry and retention section of said body.

15. The inspection tester apparatus for testing for explosives of claim 14 wherein said heater is a resistance heater.

16. The inspection tester apparatus for testing for explosives of claim 14 wherein said heater is a resistance heater that includes a resistance heating coil and a controller.

17. The inspection tester apparatus for testing for explosives of claim 14 wherein said heater is a chemical heater.

18. The inspection tester apparatus for testing for explosives of claim 14 wherein said heater is a chemical heater with a nanolaminate chemical heating element.

19. The inspection tester apparatus for testing for explosives of claim 14 wherein said heater is a chemical heater with an aluminum and nickel nanolaminate chemical heating element.

20. The inspection tester apparatus for testing for explosives of claim 14 wherein said heater is a combustion heater.

21. The inspection tester apparatus for testing for explosives of claim 14 wherein said heater is a combustion heater comprising a lighter and a connector connecting said lighter to said body.

22. The inspection tester apparatus for testing for explosives of claim 14 wherein said at least one explosives detecting reagent comprises a Griess reagent.

23. The inspection tester apparatus for testing for explosives of claim 14 wherein said at least one reagent holder and dispenser comprises an ampoule.

24. The inspection tester apparatus for testing for explosives of claim 14 wherein said at least one reagent holder and dispenser comprises a breakable ampoule.

25. The inspection tester apparatus for testing for explosives of claim 14 wherein said at least one reagent holder and dispenser comprises a breakable glass ampoule.

26. The inspection tester apparatus for testing for explosives of claim 14 wherein at least one reagent holder and dispenser comprises a breakable glass ampoule with indentations on said breakable glass ampoule.

27. The inspection tester apparatus for testing for explosives of claim 14 wherein said heater is a nanolaminate chemical heating element that includes solder, brazing material, or other form of bonding material.

* * * * *